United States Patent [19]
Wilkinson et al.

[11] Patent Number: 5,744,117
[45] Date of Patent: Apr. 28, 1998

[54] FEED PROCESSING EMPLOYING DISPERSED MOLTEN DROPLETS

[75] Inventors: Mark A. Wilkinson, Lexington; Christopher J. Nagel, Wayland, both of Mass.

[73] Assignee: Molten Metal Technology, Inc., Waltham, Mass.

[21] Appl. No.: 399,825

[22] Filed: Mar. 7, 1995

Related U.S. Application Data

[63] Continuation-in-part of Ser. No. 46,693, Apr. 12, 1993, Pat. No. 5,395,405.

[51] Int. Cl.[6] ................................................. A62D 3/00
[52] U.S. Cl. ........................... 423/563; 423/DIG. 12; 588/201; 588/205; 588/216
[58] Field of Search .................... 423/437 R, DIG. 12, 423/563; 588/201, 205, 216; 75/414, 501

[56] References Cited

U.S. PATENT DOCUMENTS

| | | | |
|---|---|---|---|
| 2,862,810 | 12/1958 | Alexandrovsky | 75/60 |
| 3,542,352 | 11/1970 | Themelis | 266/36 |
| 3,642,583 | 2/1972 | Greenberg et al. | 203/11 |
| 3,668,120 | 6/1972 | Patterson | 210/60 |
| 3,812,620 | 5/1974 | Titus et al. | 48/65 |
| 4,012,457 | 3/1977 | Bredeson et al. | 260/683 R |
| 4,085,923 | 4/1978 | Queneau et al. | 266/215 |
| 4,308,037 | 12/1981 | Meissner et al. | 423/DIG. 12 |
| 4,469,661 | 9/1984 | Shultz | 423/DIG. 12 |
| 4,511,372 | 4/1985 | Axelsson | 48/197 R |
| 4,574,714 | 3/1986 | Bach et al. | 110/346 |
| 4,602,574 | 7/1986 | Bach et al. | 110/346 |
| 4,666,696 | 5/1987 | Shultz | 423/659 |
| 4,681,599 | 7/1987 | Obkircher | 48/92 |
| 4,925,532 | 5/1990 | Meuser et al. | 202/219 |
| 5,136,117 | 8/1992 | Paisley et al. | 585/241 |
| 5,139,558 | 8/1992 | Lauwers | 65/135 |
| 5,139,568 | 8/1992 | Geiger | 75/501 |
| 5,177,304 | 1/1993 | Nagel | 588/201 |
| 5,301,620 | 4/1994 | Nagel et al. | 110/346 |
| 5,395,405 | 3/1995 | Nagel et al. | 585/240 |
| 5,396,850 | 3/1995 | Conochie et al. | 110/346 |
| 5,472,478 | 12/1995 | Brotzmann | 75/414 |
| 5,480,473 | 1/1996 | Hardie et al. | 75/501 |

FOREIGN PATENT DOCUMENTS

| | | |
|---|---|---|
| WO 92/12265 | 7/1992 | WIPO . |
| WO 93/10862 | 6/1993 | WIPO . |
| WO 94/00533 | 1/1994 | WIPO . |

*Primary Examiner*—Michael Lewis
*Assistant Examiner*—Stuart L. Hendrickson
*Attorney, Agent, or Firm*—Hamilton, Brook, Smith & Reynolds, P.C.

[57] ABSTRACT

A method and an apparatus produce a product in at least one phase from an organic component in a feed gas stream. The method includes forming a process zone including a process molten bath and a process gas space disposed over the process molten bath. Molten droplets of said molten bath are then dispersed across the process gas space. The feed gas stream is then directed into the process gas zone, wherein the organic component is exposed to said molten droplets, thereby converting at least a portion of the organic component to a product in at least one phase.

The apparatus of the invention comprises a reactor which includes a gas formation section, having a feed inlet, and means for retaining a solid feed component within the gas formation section. The apparatus also includes a process section, disposed in the reactor, having a process gas space, a gas outlet and a process molten bath disposed therein. Further, means are provided for dispersing molten droplets of said molten bath across the process gas space to expose an organic component in the feed gas stream to molten droplets.

32 Claims, 6 Drawing Sheets

FEED PROCESSING EMPLOYING DISPERSED MOLTEN DROPLETS

RELATED APPLICATIONS

This is a continuation-in-part of U.S. Ser. No. 08/046,693, filed Apr. 12, 1993, now U.S. Pat. No. 5,395,405, issued on Mar. 7, 1995, which is hereby incorporated by reference.

BACKGROUND OF THE INVENTION

Enormous amounts of various hazardous wastes are produced every year. These wastes often include organic materials, such as tires, pesticides, paints, spent resins and solvents. Currently, many of these organic wastes are disposed in landfills or by incineration. However, disposal of these wastes in landfills and by incineration has become an increasingly difficult problem because of diminishing availability of disposal space, strengthened governmental regulations, and the growing public awareness of the impact of the disposal of hazardous and non-hazardous waste upon the environment. Release of these wastes to the environment can also contaminate air and water supplies. Furthermore, disposal of these wastes without separating out valuable components or producing valuable products constitutes an economic loss of valuable chemical constituents.

Recently, many methods have been developed for reclaiming value from materials, such as hazardous waste and industrial feeds, by converting these materials within molten baths into carbon, carbon oxide gases and lower order hydrocarbons. However, these processes typically require large molten volumes to avoid short residence times. In addition, the large molten volumes, typically required to convert a feed material, are less safe due to the amounts of energy stored therein. Also, submerged tuyeres, which are often employed with large volume molten metal baths, can experience rapid wear. Furthermore, at least a portion of bulk charges of volatile feed materials will often volatilize and blow-through the molten bath without being converted.

Therefore, a need exists for a new method and apparatus to convert organic-containing feeds into benign and/or more useful substances.

SUMMARY OF THE INVENTION

The present invention relates to a method and an apparatus for producing in at least one phase from an organic component of an organic-containing feed, wherein the organic component is in a feed gas stream.

The method includes forming a process zone including a process molten bath and a process gas space disposed over the process molten bath. Molten droplets of said molten bath are then dispersed across the process gas space. The feed gas stream is then directed into the process gas zone, wherein the organic component is exposed to said molten droplets, thereby converting at least a portion of the organic component to a product in at least one phase.

The apparatus of the invention comprises a reactor which includes a gas formation section, having a feed inlet, and means for retaining a solid feed component within the gas formation section. The apparatus also includes a process section, disposed in the reactor, having a process gas space, a gas outlet and a process molten bath disposed therein. Further, means are provided for dispersing molten droplets of said molten bath across the process gas space to expose an organic component in the feed gas stream to molten droplets.

This invention has the advantage, for example, of more efficiently converting hazardous feeds to form useful hydrocarbons and/or carbon oxide gases. Additional advantages of this invention are that it provides an improved method for processing feeds using smaller molten volumes, permits the use of safer, smaller heat sources, due to the larger surface area to volume ratio of molten spray compared to a molten bath, permits the use of tuyeres which are not submerged in a molten bath, thereby reducing tuyere wear, and provides assurance that volatile hazardous feeds, which are bulk charged, will be converted to non-hazardous species prior to discharging from the apparatus.

DETAILED DESCRIPTION OF THE INVENTION

The features and other details of the apparatus and method of the invention will now be more particularly described with reference to the accompanying drawings and pointed out in the claims. It will be understood that these particular embodiments of the invention are shown by way of illustration and not as limitations of the invention. The principle features of this invention can be employed in various embodiments without departing from the scope of the invention.

Figure 1:
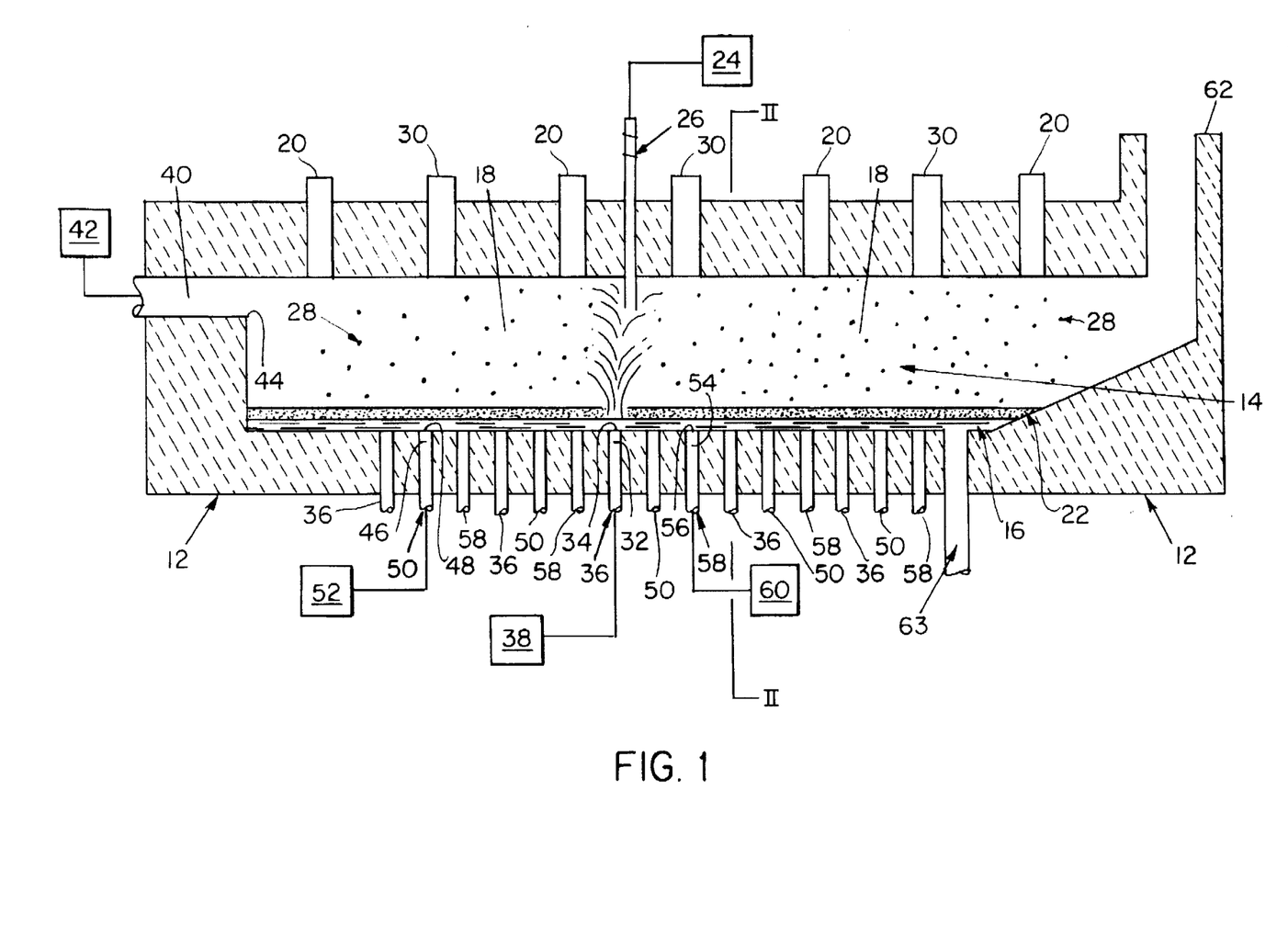
FIG. 1 is a cut-away side elevational illustration of an apparatus suitable for forming a product according to the method of the invention by directing a feed through a zone containing molten droplets.

One embodiment of an apparatus, suitable for performing the method of invention, is illustrated in FIG. 1. Said apparatus includes reactor 12, containing process section 14. The walls of reactor 12, which enclose process section 14, are refractory under the conditions within process section 14. The refractory nature of the walls of reactor 12 can be improved, optionally, by cooling the walls by means known in the art, such as water cooling.

Process molten bath 16 is disposed in the lower portion of process section 14. Process gas space 18 is disposed within process section 14 above process molten bath 16. Process molten bath 16 is formed by partially filling process section 14 with a suitable metal. The metal is then heated to a suitable temperature by activating plasma torches 20 or by other suitable means, such as induction coils, oxyfuel burners, electric arcs, and exothermic chemical reactions such as the oxidation of aluminum, carbon, carbon monoxide, hydrogen or fuel oil.

A molten bath includes, for example, at least one metal, metal oxide, metal salt, matte (e.g., FeS) ceramic material, metal alloy or metal solution, solution of metals or combinations thereof. A metal solution, as defined herein, is a metal containing a dissolved atomic non=metallic species, such as carbon or sulfur. In addition, in a solution of metals, two or more metals are codissolved in a single phase, such as solutions of iron with chromium, manganese, copper, nickel or cobalt.

The molten bath can also include a metal having a free energy of oxidation, at the operating conditions of said molten bath, which is greater than the free energy of oxidation of atomic carbon to carbon monoxide. In addition, a molten bath can include a metal having a free energy of chlorination, at the operating conditions of said molten bath, which is greater than the free energy for the chlorination of hydrogen to form hydrochloric acid.

Optionally, the molten bath can contain a metal which has a solubility for carbon, sulfur, halogen and/or oxygen. Preferably, the solubility of the molten bath for carbon, sulfur, halogen or oxygen is greater than about 0.5% by weight. Preferred molten metals for dissolving carbon, sulfur, halogen and oxygen are iron, copper, calcium and iron, respectively.

Further, a molten bath can include more than one phase of molten material, such as a molten metal phase and a ceramic phase or two immiscible metal phases, wherein the first phase supports the formation of carbon dioxide, while the second phase supports the formation of carbon dioxide from carbon monoxide. U.S. Pat. No. 5,177,304, by C. J. Nagel, discloses a method and apparatus for treating organic feeds in molten baths to forming carbon oxide gases. The teachings of U.S. Pat. No. 5,177,304 are incorporated herein by reference.

A ceramic material can be formed by directing suitable components, such as metals, metal oxides, halogens, sulfur, phosphorus, heavy metals, fluxes, sludges, etc., from flux source 24 through inlet tube 26 and onto and/or into process section 14. Said components then form oxides by exposure of the components to an oxidant or form other stable compounds by reacting with other less stable components, such as alkali metal or alkaline earth metal cations. Examples of metal oxides typically found in a ceramic material include titanium oxide (TiO), zirconium oxide ($Zro_2$), aluminum oxide ($Al_2O_3$), magnesium oxide (MgO), calcium oxide (CaO), etc. Other examples of suitable components of a ceramic material include halogens, sulfur, phosphorus, heavy metals, etc. It is to be understood that a ceramic material can include more than one metal oxide. Examples of such stable reaction products include calcium fluoride ($CaF_2$) and magnesium phosphate ($Mg_3(PO_4)_2$).

Reactor 12 further includes means for dispersing molten droplets 28 across process gas space 18, wherein the dispersion of metal droplets is substantially perpendicular to the flow path of gases through process gas space 18. Molten droplet dispersing means disperse an amount of molten droplets 28, across process gas space 18 such that substantially all organic component in a feed gas stream is exposed to molten droplets 28 prior to exiting process section 14.

A suitable molten droplet dispersing means includes a molten source, such as process molten bath 16, and a means for forming and directing molten droplets across process gas space 18, such as gas jets. In one embodiment, plasma torches 20 are suitable for use as gas jets. Plasma torches 20, which are directed onto the top surface of molten bath 16, atomize molten to form molten droplets 28 which are then dispersed, by the action of plasma torches 20, across at least a cross-section of process gas space 18 within process section 14.

Other examples of droplet forming/directing means include alternate high velocity gas jets 30 which also discharge onto the surface of process molten bath 16 to form molten droplets 28 upon impacting the surface of process molten bath 16, wherein molten droplets 28 are dispersed across a cross-section of process gas space 18. It is understood that one or more high velocity jets, specifically plasma torches 20 and/or alternate high velocity gas jets 30, can be disposed at the sides and/or top of reactor 12. In a preferred embodiment, at least two opposing gas jets are directed onto the surface of molten bath 16.

An alternate droplet forming/directing means includes gas stream tuyere 32 and gas stream inlet 34, through which a gas stream is directed into process molten bath 16, suitable to entrain and disperse molten droplets 28 across a cross-section of process gas space 18. A gas stream is directed into process molten bath 16, and then flows in a substantially upwards direction through process molten bath 16, thereby entraining molten in the gas stream to disperse molten droplets 28 in process gas space 18. Alternatively, a stream of a volatilizable fluid can be directed into process molten bath 16, wherein the volatilizable fluid stream gasifies to form a gas stream.

A suitable gas stream can include a nonreactive gas, a reactive gas, and/or a second gasifiable feed. Examples of a suitable nonreactive gas include nitrogen or argon, while a suitable reactive gas is, for example, hydrogen, oxygen and carbon monoxide. Examples of gasifiable feeds suitable for a gas stream include organic feeds wherein at least a portion of the feed, or a decomposition product of the feed, is gasifiable.

Gas stream tuyere 32 includes a gas stream inlet tube 36, which provides fluid communication between gas stream source 38 and process molten bath 16, through gas stream inlet 34. It is understood that other suitable gas introduction means, such as lances, inlets and/or any other devices capable of directing a gas or gasifiable component into molten metal, can be used in place of, or in combination with, gas stream tuyeres 32.

Figure 2:
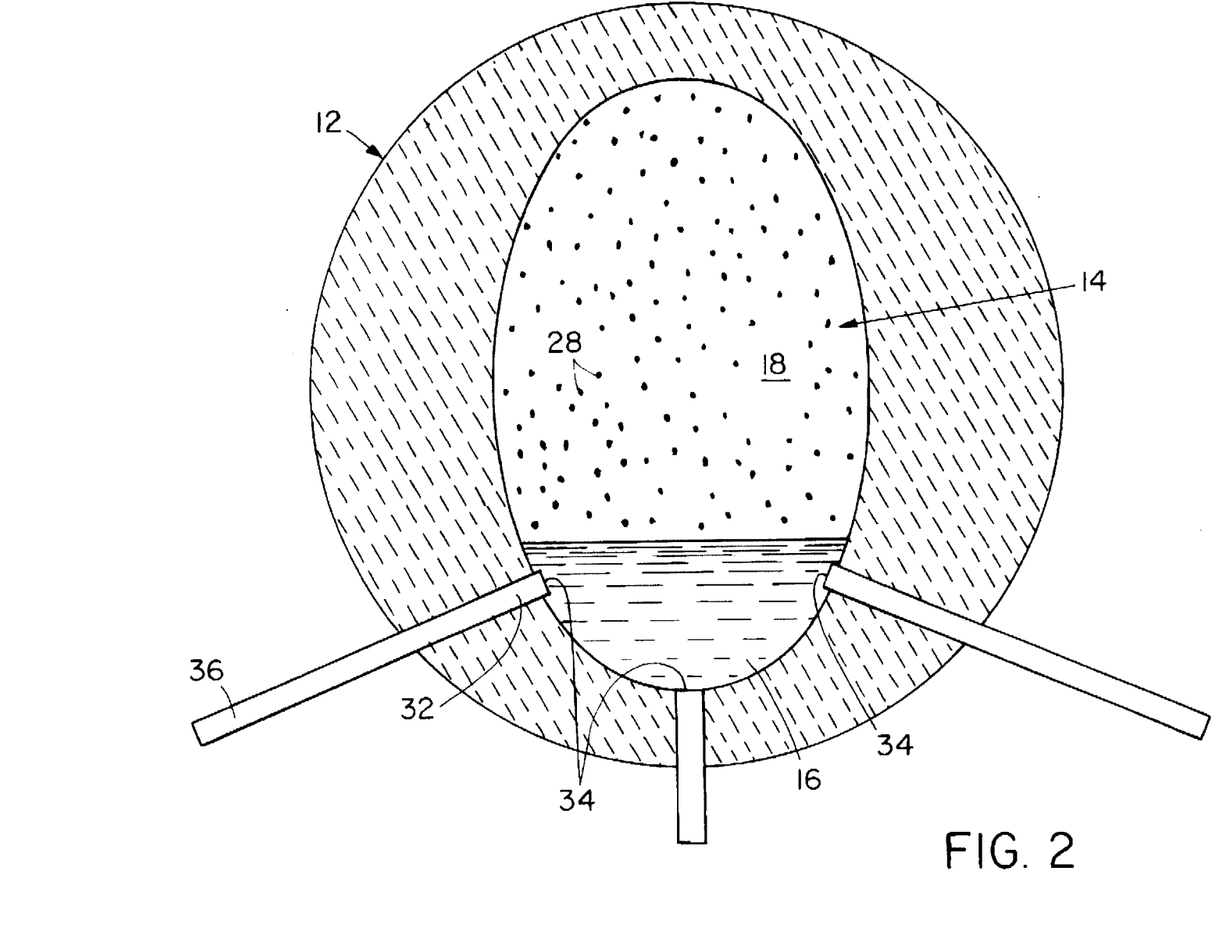
FIG. 2 is a cut-away end view illustration of the apparatus of FIG. 1 taken along line II—II.

One or more gas stream inlets 34 are disposed at the bottom and/or sides of process section 14 within process molten bath 16, in a configuration such that upon injection of a gas stream through gas stream inlets 34, molten droplets 28, which are entrained from process molten bath 16, are subsequently dispersed across a cross-section of process gas space 18. For example, as shown in FIG. 2, gas stream inlets 34 are generally disposed within a plane, which is substantially perpendicular to the flow of the gasified organic feed component through process section 14, at regular intervals of distance along the bottom and sides of process section 14.

Referring back to FIG. 1, molten droplets 28 optionally can be dispersed in process gas space 18 in the form of molten fountain 39. Molten fountain 39 contains a stream of molten droplets 28 of various sizes. A suitable molten fountain 39 is described in U.S. Pat. No. 5,395,405. Also optionally, molten droplets 28 can be formed and dispersed across a cross-section of process gas space 18 by rotating vanes, not shown, in a circular motion from near the bottom of process molten bath 16, up through process gas space 18, and then back down into process molten bath 16. As said vanes rotate, the vanes carry molten metal out of process molten bath 16 and up one side of process section 14, until molten droplets 28 fall from the vanes back into process molten bath 16. Such vanes may be attached to an independent structure contained within process section 14, or alternately, such vanes can emanate from the walls of process section 14. Said vanes would be fabricated from a refractory material, such as refractory brick.

Reactor 12 also includes means for directing an organic component in a feed gas stream into a process zone. A process zone is the zone in which the organic component is exposed to molten droplets 28, and specifically comprises process gas space 18 and molten bath 16.

A suitable feed gas stream introduction means, specifically gaseous feed inlet tube 40, extends from a portion of process section 14 above the surface of process molten bath 16, and provides fluid communication from feed gas stream source 42, through feed gas stream inlet 44, into process gas space 18 within process section 14.

It is understood that suitable directing means include, for example, tuyeres, lances, inlets and other components capable of directing gases into process gas space 18 within process section 14. In addition, one or more means of introducing a feed gas stream can direct said feed gas stream through the top, bottom and/or side walls of reactor 12 into process gas space 18.

Reactor 12 further includes a means of introducing a co-reactant into process section 14. Suitable co-reactant introduction means include co-reactant tuyere 46, which is disposed in the lower portion of process section 14. Co-reactants include, for example oxidizing agents and reducing agents. Examples of suitable oxidizing agents include, oxygen, air and compositions, substances or mixtures which can release oxygen, such as reducible metal oxides (e.g., nickel oxide, iron oxide) or carbon dioxide. Hydrogen and hydrogen-releasing compositions substances or mixtures are examples of suitable reducing agents.

Co-reactant tuyere 46 is dimensioned and configured for introducing a co-reactant into process section 14, through co-reactant inlet 48. Co-reactant tuyere 46 includes co-reactant inlet tube 50, which provides fluid communication between co-reactant source 52 and process section 14, through co-reactant inlet 48. Co-reactant inlet 48 is typically disposed in lower portion of process section 14, above the surface of process molten bath 16, at the end of co-reactant inlet tube 50. Alternatively, co-reactant inlet 48 can also be disposed below the surface of process molten bath 16 and/or in the upper portion of process section 14. It is understood that suitable co-reactant introduction means include one or more tuyeres, inlets or tubes, which can be disposed at bottom, sides or top of reactor 12.

Co-reactant tuyere 46 can be a concentric tuyere which is water-cooled. Typically, when co-reactant tuyere 46 is cooled by water injection, co-reactant inlet 48 is not immersed in process molten bath 16.

Alternately, co-reactant tuyere 46 can also be a double-concentric tuyere, which is dimensioned and configured to direct feed or a shroud gas into the process section. Feed introduced through co-reactant tuyere 46, which can consist of the feed to be converted or a second feed, can also function as a shroud gas for co-reactant tuyere 46. Further, co-reactant tuyere 46 can be a multiple concentric tuyere, which is capable of separately injecting three or more materials, such as an oxidant, shroud gas, and other materials (e.g., feed, fuels or carbon sources) into reactor 12. Co-reactant tuyere 46 can also function as a means, or optionally, as the only means, for dispersing molten droplets 28 in process gas space 18 by directing a gas stream through process molten bath 16.

Reactor 12 also includes alternate tuyere 54, and alternate inlet 56, which provide an alternate means for directing an additional substance, such as a second organic feed, a carbon source, and/or a fuel material for heating molten metal, into process molten bath 16. Alternate tuyere 54 includes alternate inlet tube 58, which provides fluid communication between additional substance source 60 and process molten bath 16, through alternate inlet 56. It is understood that alternate directing means include one or more tuyeres, lances or tubes, which can be disposed at the bottom, sides or top of reactor 12.

Gas outlet 62, which extends from upper portion of process section 14, is suitable for conducting a product gas from process gas space 18 out of reactor 12.

Bottom tap 63 extends from the lower portion of process section 14, below the surface of process molten bath 16. Bottom tap 63 is suitable for removing one phase of molten material from reactor 12. Additional drains may be provided as a means of removing continuously, or discretely, additional phases of molten materials from reactor 12. Material can also be removed from process section 14 by other methods, such as are known in the art.

In the method of this invention, an organic component within a feed gas stream is converted in process section 14 to form a product in at least one phase. A suitable organic component can include gasified organic molecules, carbon oxide gas and a dispersion of carbonaceous particles suspended in a gas stream. A feed gas stream can also include other components such as hydrogen, water and inorganic chemicals containing sulfur, phosphorous, volatilizable heavy metals, nitrogen and combinations thereof.

A product can be in one or more phases. Specifically, in the gas phase or in a condensed phase. Examples of gas phase products include small hydrocarbons, carbon oxide gas, carbon black gaseous oxidation or reduction products of a feed, or a mixture thereof, in addition to other components, such as hydrogen, water and inorganic gases. Small hydrocarbons are those saturated and unsaturated hydrocarbons containing up to about six carbon atoms, such as methane, ethane, ethene, butane, butene, cyclohexane and benzene. Carbon oxide gas includes carbon monoxide, carbon dioxide or a mixture thereof.

A condensed phase substance, as defined herein, is a substance in a particulate dissolved, or liquid state typically contained within process molten bath 16. Examples of condensed phase products include for instance, carburized iron, calcium chlorides, FeS matte, iron oxide and hexadecane.

In this method, a process zone is formed within process section 14, by heating process molten bath 16 with plasma torches 20, or with other suitable heating means, and by dispersing molten droplets 28 across gas space 18 above process molten bath 16. It is preferred that metal droplets 28 be dispersed approximately uniformly across gas space 18.

In one embodiment, directing the discharge of a high velocity jet, such as plasma torches 20, toward or into the surface of process molten bath 16 causes molten metal to atomize, forming molten droplets 28, and then scatters molten droplets 28 at least across process gas space 18.

In an alternate embodiment, molten droplets 28 are formed and dispersed across process gas space 18, within process section 14, by directing a gas stream through one or more gas stream inlets 34 into process molten bath 16, wherein the gas stream is substantially directed towards process gas space 18. Molten metal is then entrained in the gas stream and directed into process gas space 18, thereby forming molten droplets 28 which are dispersed at least across a cross-section of process gas space 18.

A process zone is suitable if a substantial portion of the organic component in the feed gas stream is converted to a product. Typically, an organic component is converted at temperatures at about 1200° C. or more if the organic component is within the process zone for about 1-2 seconds. Process time to convert an organic component in a process zone can be further controlled by adjusting the temperature or pressure within the process zone. Reactors, in the method of invention, can be operated at elevated pressures, atmospheric pressure or reduced pressures.

Lower temperatures within the process zone, such as below about 900° C., are typically used to cause minimal degradation of a gasified organic feed component. Higher temperatures within the process zone, such as about 900° C., are typically used to further degrade a gasified organic feed component.

Further, when treating an organic component, using heat transferred from process molten bath 16 and/or molten droplets 28, the temperature of process section 14 can be adjusted by varying the composition of process molten bath 16. For instance, lower temperature molten baths, generally having a temperature less than about 1200° C., can be formed using tin, zinc, aluminum, sodium carbonate or copper as the principal constituent of the molten metal. Additionally, higher temperature molten baths, typically having a temperature greater than or equal to about 1200° C., can be formed using manganese, nickel, cobalt, iron, chromium or aluminum oxide as the principal constituent of the molten metal.

When directed into process section 14, substantially all of the organic component in the feed gas stream is exposed to molten droplets 28 to typically form a hydrocarbon gas and/or carbon.

In an additional embodiment, a co-reactant is directed into process section 14 wherein the co-reactant then reacts with the organic component, or hydrocarbon gas, to form a product gas, such as a carbon oxide gas. For example, where an oxidant is used as the co-reactant, the oxidant is directed as the co-reactant from a co-reactant source 52 through co-reactant inlets 48 into process molten bath 16. Upon injection, the oxidant reacts with oxidizable components contained in process section 14 to form gasified oxides such as carbon monoxide, carbon dioxide, sulfur dioxide and water. Any carbon oxide gas, formed in process molten bath 16, then migrates into process gas space 18.

It is understood that a gasified organic feed component and a co-reactant can be introduced into the reactor continuously, sequentially or intermittently.

In a further embodiment, an oxidizing agent or reducing agent is introduced according to the method and system described in U.S. patent application Ser. No. 08/041,772, filed Apr. 2, 1993, which discloses the reduction or oxidation of dissolved atomic constituents of a feed in a molten bath. The teachings of U.S. patent application Ser. No. 08/041, 772, regarding the method for oxidizing and reducing dissolved atomic constituents, are incorporated herein by reference.

A product gas is then directed out of upper portion of reactor 12 through gas outlet 62. A condensed phase product can be removed from reactor 12 through bottom tap 63.

Figure 3:
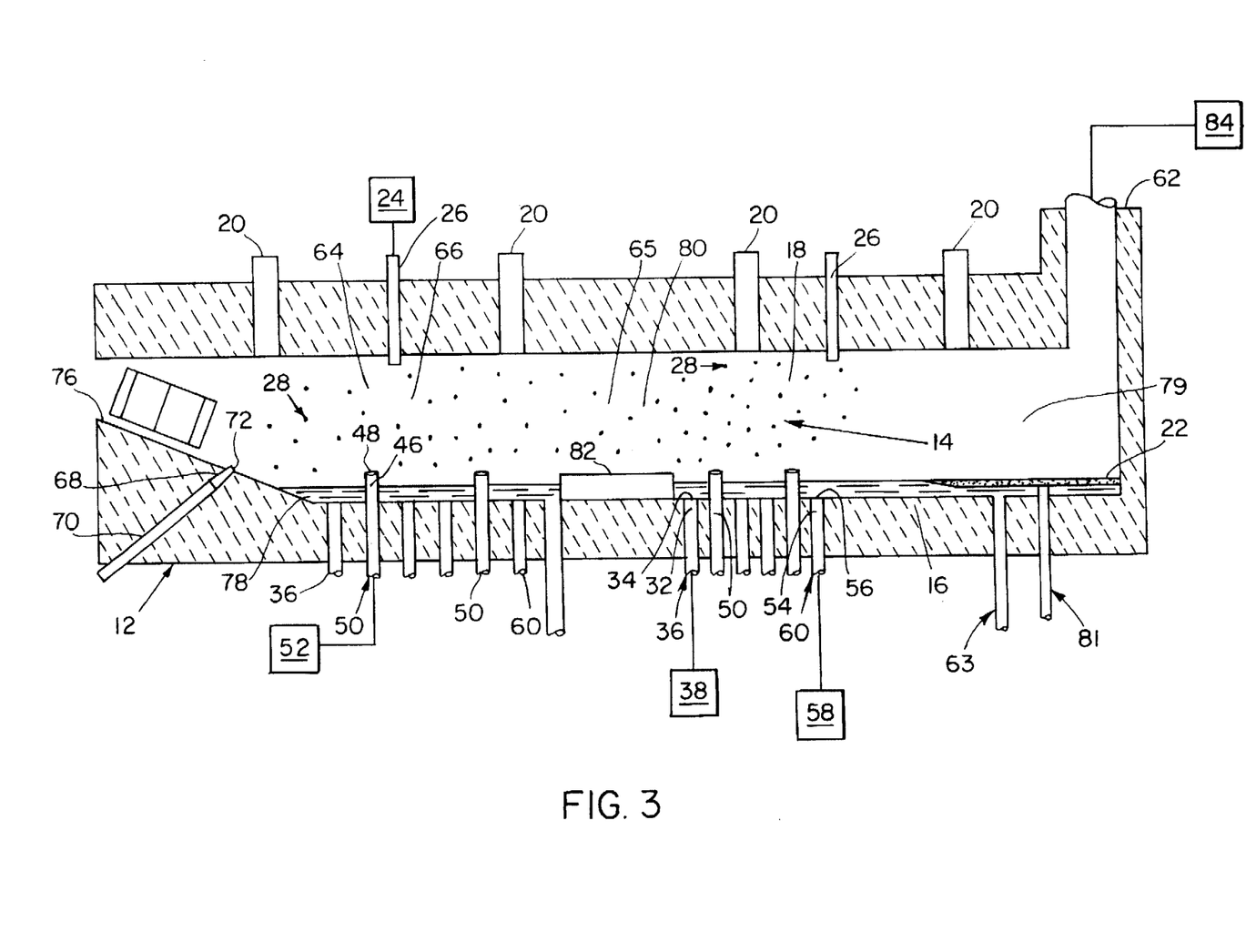
FIG. 3 is a cut-away side elevational illustration of an apparatus of the invention suitable for forming a product by directing a feed through a zone containing molten droplets.

FIG. 3 illustrates yet another embodiment of the apparatus and method of this invention. The apparatus of FIG. 3 has many of the same elements of FIG. 1 and like elements are designated with like numerals. Said apparatus includes reactor 12, containing gas formation section 64 and process section 14, which are interconnected by a suitable means 65 for retaining solid feed in gas formation section 64, while permitting gaseous flow, and optionally liquid flow, from gas formation section 64 into process section 14.

Figure 4:
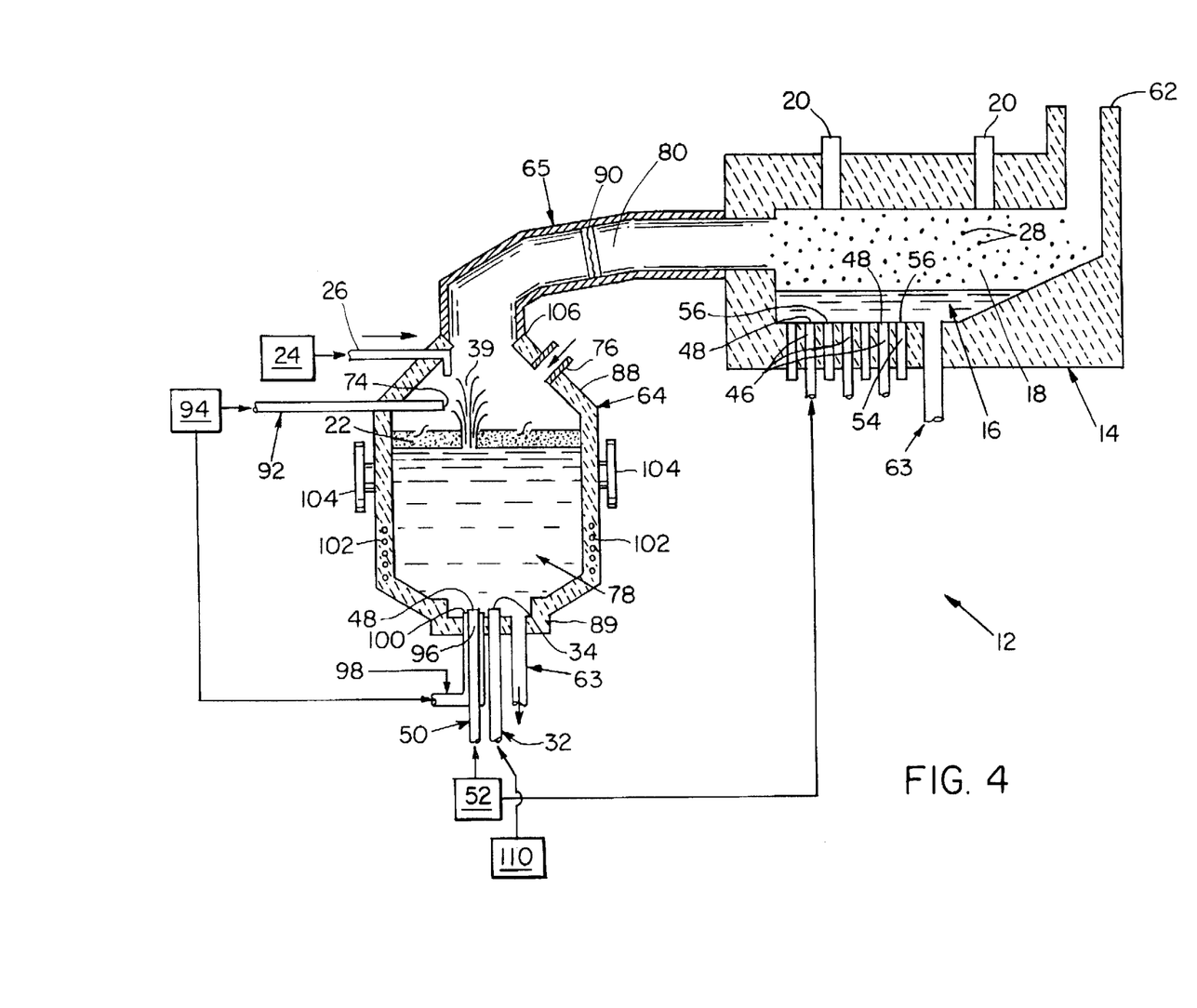
FIG. 4 is a cut-away side elevational illustration of an alternative embodiment of an apparatus of the invention suitable for forming a product by directing a feed through a zone containing molten droplets.

Gas formation section 64 and process section 14 can be different modules of a single combined unit (shown in FIG. 3) or can also be separate, distinct components (shown in FIG. 4). The wall enclosing gas formation section 64 can be a part of a single unitary wall, which also encloses process section 14, or can be a separate wall section made of the same or of different materials from the wall of process section 14. The walls enclosing gas formation section 64 are substantially refractory under the conditions within gas formation section 64. Likewise, the walls enclosing process section 14 are also refractory under the conditions within process section 14. The refractory nature of the walls can be improved, optionally, by cooling the walls using means known in the art, such as water cooling.

Examples of suitable gas formation sections 64 are shown in FIGS. 3 and 4. Other apparatus, suitable for use as gas formation section 64, include apparatus for treating a feed material to form a carbon oxide gas or hydrocarbon, such as the apparatus described in U.S. Pat. No. 5,177,304, issued Jan. 5, 1993, which discloses a method and apparatus for forming carbon dioxide from carbonaceous materials in a molten metal bath of immiscible metals, and in U.S. Pat. No. 5,489,734, which discloses a method and apparatus for producing a non-radioactive carbon oxide gas by treating a radioactive feed in a molten metal bath; U.S. Pat. No. 5,435,982 which discloses a method and apparatus for dissociating at least a portion of a feed to its atomic constituents in packed bed reactor to form product gases; and U.S. Pat. No. 5,395,405, which discloses a method and apparatus for producing a hydrocarbon gas by contacting an organic feed with a molten droplets 28. The teachings of U.S. Pat. No. 5,435,982 regarding an apparatus for treating a feed material to form a carbon oxide gas or hydrocarbon, are incorporated herein by reference.

Returning to FIG. 3, gas formation section 64 contains gas formation gas space 66, means for introducing an organic-containing feed into gas formation section 64, and means for forming a feed gas stream containing an organic component of said feed when in gas formation section 64.

A first suitable feed introduction means, specifically nozzle 68, is disposed at lower portion of gas formation gas space 66. Nozzle 68 provides fluid communication between a fluid feed source, not shown, and gas formation section 64 through fluid feed supply line 70 and fluid feed inlet 72. Fluid feed inlet 74 is disposed in gas formation gas space 66 at the end of nozzle 68.

A second suitable feed introduction means, specifically bulk feed inlet 76, which extends from reactor 12, provides a means for directing bulky feed into gas formation section 64.

It is understood that suitable means for introducing feed into various areas of gas formation section 64 include tuyeres, lances, inlets and other components capable of introducing bulk and/or non-bulk feed into gas formation section 64. In addition, suitable means of introducing feed can direct feed into gas formation section 64 through the top, bottom and/or side walls of the reactor. Furthermore, one or more means of introducing feed into gas formation section 64 can be disposed at the top, bottom and/or sides of reactor. A method and apparatus, for top charging a solid feed into a molten metal bath, are disclosed in U.S. Pat. No. 5,491, 279, the teachings of which, regarding charging a solid feed, are incorporated herein by reference. Furthermore, a lance for injecting an organic fed into a molten metal bath, and its method of use, are disclosed in U.S. Pat. No. 5,443,572, the teachings of which are incorporated herein by reference.

Suitable gas forming means for forming the feed gas stream, in gas formation section 64, include heating means and/or means for including particles of the organic component within a gas stream. Heating means can employ direct heating and/or indirect heating of the feed within a gas formation zone. Means for direct heating include, for instance, induction coils, oxyfuel burners, electric arcs, plasma torches and exothermic chemical reactions such as the oxidation of aluminum, carbon, carbon monoxide, hydrogen or fuel oil, which directly heat gas formation section 64 and feed, thereby gasifying an organic feed component. Means for indirect heating include, for example, a molten bath and/or molten droplets, which are heated using direct heating means and which then transfer heat to the feed upon exposure to said feed.

Means for including particles in a gas stream include combustion of the feed with an oxidant, wherein the oxidant is injected into gas formation section 64 through co-reactant tuyere 46, such as to form smoke. Alternate means includes pyrolysis of the feed by heating the feed with heating means, concurrent with, or followed by, directing a gas stream, such as a non-reactive gas through gas stream tuyere 32 into gas formation section 64, such as by entraining a dispersion of carbonaceous particles, formed by pyrolysis, within a stream of nitrogen gas. Further, means for including particles in a gas stream also include directing a gas stream through a feed which is already in the form of carbon-containing particles.

A gas formation zone, as defined herein, is the area within gas formation section 64 in which feed is converted to the feed gas stream. The gas formation zone includes gas formation gas space 66, and depending upon the type of gasifying means employed and the location and type of feed converted, can also possibly include gas formation molten bath 78 and, optionally, a ceramic layer 22 which is disposed upon gas formation molten bath 78.

Suitable heating means, when employed as the gas forming means, are capable of heating feed over a temperature range having a lower temperature limit, corresponding to a temperature at which an organic feed component gasifies or decomposes to produce the desired organic decomposition products, and having an upper temperature limit, corresponding to a temperature at which the reactor walls enclosing gas formation container remain refractory. Typically, heating means are capable of heating the gasified organic feed component, and its feed precursor, to a temperature between about 100° C. to about 2800° C. Lower temperatures, such as below about 900° C., are typically used to volatilize an organic component of the feed, or to cause minimal degradation of the organic feed component, or to prevent gas formation of metals contained within the feed. Preferably, to form a hydrocarbon gas, the effective temperature of the gasified organic feed component is between about 900° C. and about 1100° C. Higher temperatures, such as higher than about 1300° C., are typically used to further degrade a feed.

Though having molten metal is required in process section 14 (e.g., molten droplets 28 and process molten bath 16), the presence of molten metal in gas formation section 64, other than that derived from gasifying feed, is optional.

In an optional embodiment wherein said gasifying means includes gas formation molten bath 78, gas formation molten bath 78 is disposed in the lower portion of gas formation section 64. Gas formation molten bath 78 can be formed by partially filling gas formation section 64 with a suitable metal and then heating the metal to a suitable temperature by activating plasma torches 20 or by other means, not shown.

Plasma torches 20, which are disposed in the upper portion of reactor 12, are suitable for maintaining gas formation molten bath 78 in a molten state at a temperature suitable to form the desired gasified organic feed component. Plasma torches 20 are also suitable for atomizing molten metal to form molten droplets 28 which are dispersed, by the action of plasma torches 20, within gas formation gas space 66.

At least a portion of the molten metal, present in process section 14, and if provided in gas formation section 64, is typically in the form of a molten bath. When present in both sections, a molten bath can either comprise a single, unified molten bath which flows between gas formation section 64 and process section 14 through the retaining means, or two separate molten baths having substantially the same composition, or two separate molten baths having different compositions. Optionally, gas formation section 64 and/or process section 14 can include a ceramic phase, which is mixed in the molten bath as a result of the action of the molten droplet dispersing means. In an embodiment wherein process molten bath 16 includes a ceramic phase and at least one molten metal phase, reactor 12 optionally includes settling section 79 which is disposed between process section 14 and gas outlet 62. Within settling section 79, the metal phase and the ceramic phase of process molten bath 16 will separate to form ceramic layer 22 which is disposed on top of process molten bath 16. Ceramic layer 22 can be removed from reactor 12 separately from process molten bath 16 by draining through ceramic tap 81. Another example of a reactor having a process section and a settling section, with means for separating removing different molten phases, such as molten metal and a ceramic phase, is disclosed in U.S. Pat. No. 5,301,620, issued Apr. 12, 1994. U.S. Pat. No. 5,301,620 is incorporated herein by reference.

Disposed within reactor, and interconnecting gas formation section 64 and process section, is means for substantially retaining solid feed within gas formation section 64. Said retaining means also concurrently directs a gasified organic feed component, and optionally liquids such as molten metal, from gas formation section 64 through flow section 80 and into process section 14. Retaining means 65, which permits the flow of gases and liquids, functions as a plug flow zone.

Retaining means 65 includes flow section 80 and retainer 82, wherein the retainer blocks the flow of non-gasified solids from gas formation section 64 into process section 14. Retainer 82 can be disposed at the entrance to flow section and/or within flow section 80. Further, a retainer can either entirely, or partially, or not at all block the cross-section of flow section 80, which is substantially perpendicular to the flow path of gases through flow section 80. Wherein retainer 82 does not at all block the cross-section of flow section 80, the bottom of said flow section must be elevated above the top surface of any liquids to thereby retain solid feed within gas formation section 64, as shown in FIG. 4.

Retaining means 65 is suitable if it substantially precludes the transport of solid feed into process section with the exception of small particles condensed phase component which can pass through openings in the retainer, and which particles are typically fully converted within process section 14 to a product in at least one phase.

A condensed phase component, as defined herein, includes particulates, dissolved solids and liquids contained in gas formation molten bath 78 which are then transported into process molten bath 16, by molten bath flow through retainer 82. Condensed phase component particulates can include small feed particles and particles resulting from the conversion of the feed to form the feed gas stream.

Examples of suitable retainers 82 include porous plugs, a wall of refractory bricks, a filter or a gas formation compartment's reactor wall, wherein the retainer is disposed between gas formation section 64 and process section 14, wherein the retainer extends from about the bottom of gas formation section 64, or of flow section, to a level above the top of a gas formation molten bath or liquid feed product contained, or which can possibly be formed, in gas formation section 64. Thus, the level of the molten metal contained in gas formation molten bath 78 is below the top of retainer 82. In these examples, only the feed gas stream can flow over the retainer when directed from gas formation section 64, through flow section 80 and into process section 14 thereby sealing, process molten bath 16 from gas formation molten bath 78.

Other examples of other suitable retainers, which entirely block said flow section cross-section, and allow gaseous and molten bath flow, but no substantial solid feed flow, include at least one filter, porous plug, slotted wall, orifice or throat across or over which gaseous flow must pass when directed from gas formation section 64, through flow section 80 and into process section 14. Examples of suitable porous plugs include aluminum oxide plugs having ¼ inch holes drilled through the plugs to allow flow through the plugs.

Optionally, flow section 80 can contain two retainers (not shown), each entirely blocking the cross-section of said flow section, having disposed between the two retainers a means for purifying the feed gas stream. Purification means include physical purification means, such as for removing small particulates and also chemical purification means, such as for removing at least a portion of some chemical impurities from the gasified organic feed component. For example, to remove halogens from gasified hydrocarbons or carbon oxide gases, a bed of calcium oxide pellets is disposed between the two retainers, through which the gasified organic feed component must flow, thereby removing halogens from said gasified feed component.

Reactor 12 also includes means for directing the feed gas stream from the gas formation gas space 66, through porous plug 82, and then into process gas space 18, wherein the organic component in the feed gas stream is exposed to one or more molten droplets 28 to form at least one product in at least one phase. Any product gas is subsequently discharged out of process gas space 18.

Said feed gas stream directing means includes gas outlet 62 for directing gases out of process gas space 18 within process section 14, wherein gas outlet 62 is disposed in a wall of reactor 12 enclosing process gas space 18. The feed gas stream directing means also includes a means for creating a differential pressure between the gases in gas formation gas space 66, the gases process gas space 18, and the gases on the discharge side of the gas outlet 62. Means for creating a differential pressure can include, for example, gasifying means employed within gas formation section 64, means for directing gases into gas formation section 64 such as an oxidant and/or an entraining gas stream, means for condensing gases discharged through gas outlet 62, retaining means which constrict the flow of gases from gas formation section 64 to process section, and a blower taking a suction on process gas space 18.

In another embodiment, reactor 12 includes a means of introducing a co-reactant into gas formation section 64 and/or into process section 14. Suitable co-reactant introduction means include one or more tuyeres, inlets or tubes, which can be disposed at bottom, sides or top of reactor. Suitable co-reactant introduction means include co-reactant tuyeres, 32 which are disposed in the lower portions of gas formation section 64 and/or process section 14.

It is preferred the oxygen be directed into a molten bath within the gas formation section and within the process section.

Wherein feed is also introduced through co-reactant tuyere 46, the inclusion of a separate means for introducing non-bulk feed into gas formation section is optional. Further, a co-reactant tuyere 46 can also function as a means, or optionally the only means, for dispersing molten droplets 28 in a gas space.

In another embodiment, reactor 12 further includes one of more additional components 84 for further treating product gas and/or molten metal. Additional components 84 for treating a product gas include, for example, means for further converting product gas by exposure to additional molten droplets 28, means for quenching reactions within product gas, means for purifying product gas, and regenerator furnaces. Additional components 84 for treating molten metal include, for example, means for separating slag from molten metal and means for producing high quality condensed phase products, such as a counter flow, plug flow furnace, etc.

Means for purifying a product gas include means for chemical and/or physical separation of impurities from product gas. Physical separation means include means for removing particulates and volatilized heavy metals from product gas. It is known that purification means can be disposed upstream, downstream or in gas outlet 62. Physical and/or chemical purification means can also be included in retaining means, disposed between gas formation and process sections.

Means for separating particulates include filters, packed beds, horizontal baffles, vertical baffles, centrifugal separators, cyclone separators and any other means known in art of separating a particulate impurity from a gas stream.

Figure 5:
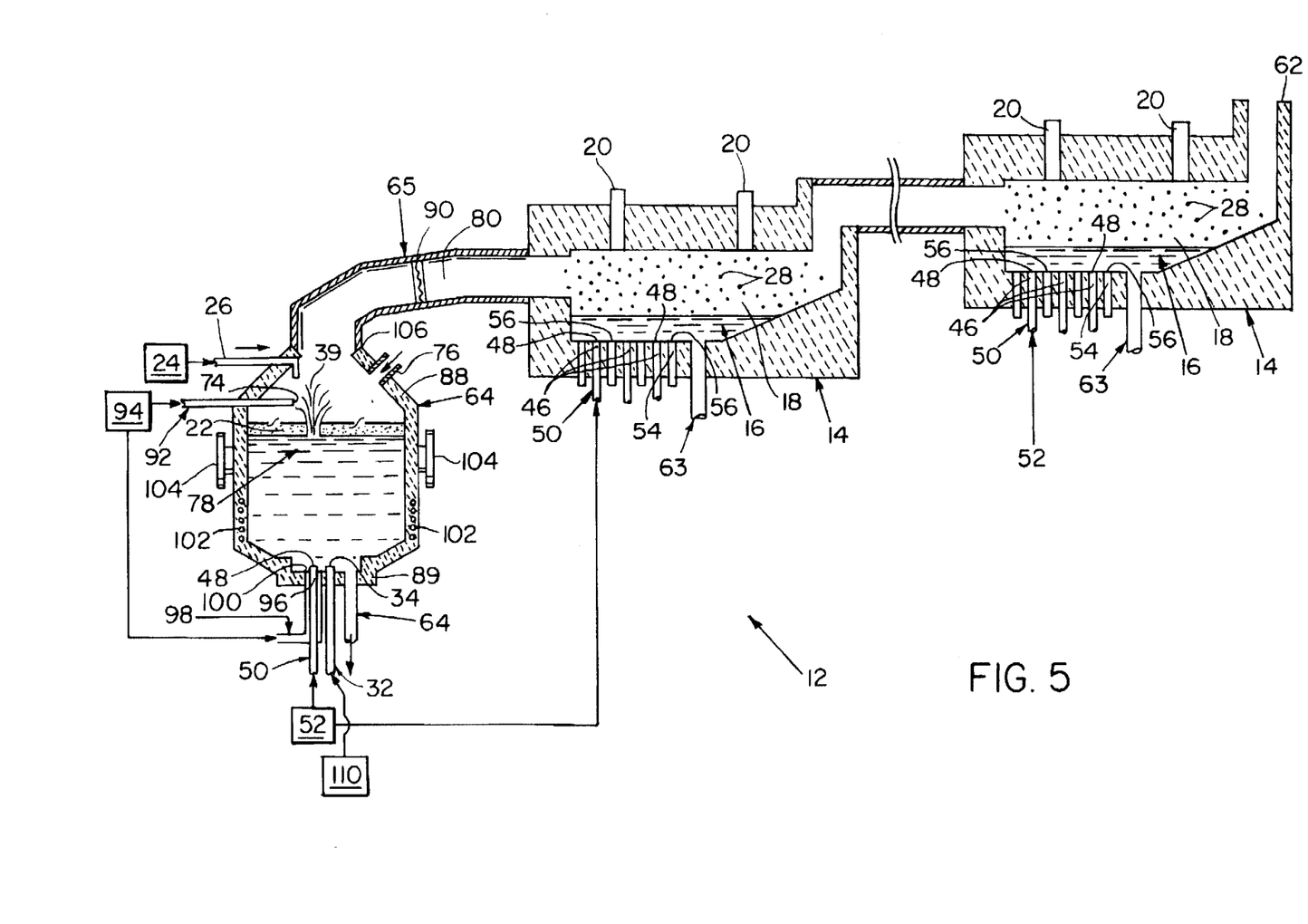
FIG. 5 is a cut-away side elevational illustration of another embodiment of an apparatus of the invention suitable for forming a product by directing a feed through a zone containing molten droplets.

Other physical separation means include means for scrubbing out impurities from a product gas, such as volatilized heavy metals or chlorine, for example a zinc splash condenser or a second process section, as shown in FIG. 5. When used to condense volatilized heavy metals, such as iron vapor from the first process molten bath, a molten bath, a lower temperature metal at a temperature below condensation temperature of iron, e.g. tin or zinc, is used in the second process section. In another embodiment, wherein the second process section is used to scrub chlorine from a gas product directed into a second process section from a first process section, the second process molten bath includes calcium, typically at a temperature between about 1400° C. to 1700° C.

Chemical separation means include means for removing chemical impurities, such as halogens and hydrogen halides. Examples of suitable chemical separation means include baffles, calcium oxide packed beds, scrubbers and a second process section having a molten bath containing tin or zinc, which is suitable to scrub halogens from product gas.

In an alternative embodiment, a means for rapidly cooling product gas is provided to control chemical reactions and degradation of desirable short-chain hydrocarbons in the off-gas, as is disclosed in U.S. Pat. No. 5,585,532.

In another embodiment, a processing unit is provided to convert components of the product gas, such as hydrocarbons, halogens or sulfur dioxide, into a desired final product. A suitable processing unit, for example, includes regenerator furnaces which convert hydrocarbons to ethylene, halogens to hydrogen halides, or sulfur dioxide to sulfuric acid, by means known in the art.

In the method of this invention, as shown in FIG. 3, a feed is converted to form a feed gas stream, containing an organic component of the feed, and optionally a condensed phase component within gas formation section 64. Said feed gas stream, and optionally condensed phase component, is then converted to form a product gas in at least one phase within process section 14.

Typically, feed contains an component, which can be formed into a feed gas stream, and which then can be converted to generate a product in at least one phase, which is substantially separated from a solid component of the feed. A solid feed component comprises a feed component, which has not yet formed a feed gas stream and which is substantially sealed from the process zone by retaining means 65.

A feed is gasifiable if upon heating or oxidation, optionally with the introduction of a gas stream into the fed, under conditions of gas formation section 64, feed component volatilizes, or decomposes, into volatilizable intermediates which then volatilize, and/or react with a co-reactant to form gaseous co-reactant reaction products and/or is suspended as dispersed particles within a gas stream.

A feed gas stream of this invention can include, for example, gasified organic molecules, carbon oxide gas, carbonaceous particles and other components such as hydrogen, water, sulfur dioxide, phosphorous, volatilizable heavy metals and halogen atoms.

A condensed phase component of this invention can include small feed particles, feed decomposition and reaction products, such as carbon, sulfur, calcium chloride and iron sulfide.

A feed component is non-gasifiable if upon heating or oxidation, under conditions of gas formation section 64, feed component will remain solid and can not be suspended in a suitable gas stream.

A feed can contain a gasifiable and/or non-gasifiable inorganic component, such as a metal, metal salt, halogen, sulfur, phosphorus, nitrogen etc. A gasified inorganic component, for example, metal, sulfur or halogen, can be subsequently separated, either chemically and/or physically, from product gas.

Preferably, a feed includes at least one organic chemical. Feed typically consists of a single organic component or of multiple components. A multiple component feed can include a mixture or solution of various organic components, and possibly also inorganic components. A multiple component feed can additionally include a compound wherein an organic and inorganic component are chemically bound, such as an organometallic compound. Further, a multiple component feed can include an amalgam in which various feed components are physically bound, such as a plastic impregnated with metal particles.

A wide variety of feed materials is suitable for process by this invention. Examples of suitable feeds include any organic chemicals such as plastics and polymers; halogenated organic chemicals such as chlorobenzenes, polyvinyl chlorides, polychlorinated biphenyls and polytetrafluoro ethylene; metal-bearing organic feeds, contaminated organic feeds such as spent organic solvents, spent organic acids, coke feeds, petroleum residuals, inner tubes and tires; and radioactively contaminated organic feeds such as medical feed, spent ion exchange resins and $Co^{60}$ contaminated fabric.

Feeds convertible by an apparatus of this invention are typically solids or fluids prior to being directed into apparatus.

In this method, shown in FIG. 3, a gas formation zone is formed within a gas formation section 64, by suitable means, such as by heating gas formation gas space 66 with plasma torches 20 or by forming gas formation molten bath 78. A feed is then injected into the gas formation zone within gas formation section 64. The feed is typically introduced into the gas formation zone as a bulk solid, particulate solid, or a fluid. It is understood that the feed can be directed into at least one portion of a zone, specifically gas formation gas space 66, gas formation molten bath 78, and/or optionally a ceramic layer 22. Upon injection, the feed is exposed to suitable gas forming means and gasifies, and/or decomposes and is then gasified, and/or is suspended as a particulate in a gas stream, to form a feed gas stream, and optionally, forms a condensed phase component.

In one embodiment, the feed is contacted with an oxidant, directed into gas formation section 64 through co-reactant tuyere 32, and is combusted to form a feed gas stream.

In the embodiment wherein feed is gasified, by contacting the feed with molten droplets 28 dispersed within gas formation gas space 66, the dispersion of droplets 28 is not required to be across an entire cross-section of gas formation section 64. For instance, gas formation section 64 could employ a single molten fountain, as described in U.S. Pat. No. 5,395,405, to gasify the feed.

Alternatively, the feed can be directed into gas formation molten bath 78, wherein feed is heated to form a gasified organic feed component, wherein said gasified component then migrates from gas formation molten bath 78 into gas formation gas space 66 as a feed gas stream. The feed gas stream gasified organic feed is then directed into process section 14 for conversion to desired product.

In one embodiment of the method of invention, a fluid feed is directed into gas formation molten bath 78 by injecting the feed into gas formation section 64. The fluid feed is directed from fluid feed source, not shown, through fluid feed supply line 70, into nozzle 68 which discharges through fluid feed inlet 72 into gas formation molten bath 78. Upon injection of the fluid feed, the feed gasifies, and/or is decomposed and partially gasifies, and/or is oxidized or reduced, to form a gasified organic feed component.

In an alternate embodiment, where the feed is bulky, the feed is directed through bulk feed inlet 76 into upper portion of gas formation section 64.

The feed gas stream then flows, due to differential pressure, from gas formation section 64, across retaining means 65, and into process gas space 18 within process section 16. Concurrently, solid non-gasified feed is substantially retained within gas formation molten bath 78, in gas formation section 64, by retaining means 65.

Within process section 16, the discharge of plasma torches 20 are directed into gas formation molten bath 78 to heat and atomize the molten metal and disperse molten droplets 28 across a cross-section of process gas space 18.

The feed gas stream from gas formation section 64 is then exposed to molten droplets 28, whereupon the organic feed component is converted, optionally by reacting with a co-reactant, to form a product in at least one phase. Any product gas is then directed out of upper portion of reactor 12 through gas outlet 62. Condensed phase product is removed through bottom tap 64 and/or ceramic tap 81.

When heating feed (or feed component within a feed gas stream) by using a molten bath and/or molten droplets, the temperature of the subject section can be adjusted by varying the composition of molten bath. For instance, lower temperature molten baths, generally having a temperature less than about 1200° C., can be formed using tin, zinc, aluminum, sodium carbonate or copper as the principal constituent of the molten metal. Additionally, higher temperature molten baths, typically having a temperature greater than or equal to about 1200° C., can be formed using manganese, nickel, cobalt, iron, chromium or aluminum oxide as the principal constituent of the molten metal.

In another embodiment, an oxidant is directed as the co-reactant from a co-reactant source 52 through co-reactant inlets 48 into reactor 12. Oxidant can be directed into either, or both, gas formation section 64 and process section 16. Upon injection, the oxidant will react with the feed components contained in process molten bath 16 and/or gas formation molten bath 78, which are oxidizable, to form oxides, such as carbon monoxide, carbon dioxide and/or sulfur dioxide. Any gasified oxides then migrate into gas formation gas space 66 and/or process gas space 18. Furthermore, upon injecting an oxidant into reactor 12, oxidizable decomposition products contained in gas formation gas space 66 or process gas space 18 can also react with the oxidant to form oxides, for example, carbon oxide gas and water.

Wherein feed is introduced through co-reactant tuyere 46, the inclusion of a separate means for introducing non-bulk feed into gas formation section 64 is optional. Further, a co-reactant tuyere 46 can also function as a means, or optionally the only means, for dispersing molten droplets 28 in a gas space.

In an alternative embodiment, feed and oxidizing agent or reducing agent are introduced according to the method and system described in U.S. patent application Ser. No. 08/041,772, filed Apr. 2, 1993, which discloses the reduction or oxidation of dissolved atomic constituents in a molten bath.

The method of invention can further be used to convert a feed to form a carbon oxide gas and hydrogen gas, in combined or separate streams. This method employs a molten bath for destroying feed by dissociating feed to form various products, such as the Bach/Nagel method disclosed in U.S. Pat. Nos. 4,574,714 and 4,607,574.

In one embodiment, a bulk or non-bulk feed is directed into gas formation molten bath 78 and/or gas formation gas space 66, which are disposed within a gas formation section 64. The feed is then exposed to gas formation means, such as gas formation molten bath 78 or molten droplets 28, which are dispersed in gas formation gas space 66, formed by impacting the discharge of plasma torches 20 upon the surface of gas formation molten bath 78. Upon said exposure, at least a portion of the organic component of the feed either volatilizes and/or decomposes to form smaller volatilized hydrocarbon gases or other feed decomposition products.

The relative amounts of decomposition of the feed is a function of the type of feed treated, and the temperature of the gasified organic feed component within gas formation section 64. An increase in temperature, will typically increase the amount of feed decomposition while concurrently decreasing the formation of relatively larger gasified hydrocarbons.

After the start of gas formation, gas formation gas space 66 will contain gasified hydrocarbons and/or hydrogen gas as components of the gasified organic feed component. The gasified organic feed component is then directed through retaining means 65 into process gas space 18, which is disposed with process section 14, wherein the gasified organic feed component is then directed through a cross-section of said gas space and is exposed to molten droplets 28, disposed therein.

Upon exposure to molten droplets 28 within process section 14, hydrocarbons in the gasified organic feed component further decompose in process gas space 18.

In an alternative embodiment a radioactive feed is decomposed within gas formation molten bath 78 in gas formation section 64, using the method for treating radioactive feeds described in U.S. Pat. No. 5,489,734. The teachings of U.S. Pat. No. 5,489,734, regarding a method for treating a radioactive feed, are incorporated herein by reference.

The method of invention can also convert feed to form short-chain unsaturated hydrocarbons, such as alkenes. A gasified organic feed component, which includes a saturated hydrocarbon, is formed by gasifying a feed containing a suitable organic component within gas formation section 64. Examples of typical organic-containing feeds include "dirty" crude oil, bottoms from refineries, oil shales, hazardous feeds, feed plastics, etc. Suitable organic components contained within the feed include alkyl and aryl compounds (or substituents) such as methane, n-hexane, polyethylene, polyvinyl chloride, polyethylene terephthalate, nylon, polymethyl methacrylates and mixed plastics. The gasified organic feed component is then directed from gas formation gas space 66, through retainer 82 and into process gas space 18, wherein the gasified organic feed component is then exposed to molten droplets 28, disposed therein. Retainer 82 permits the flow of gasified organic feed component into process section 14 but keeps any significant amount of solid feed from entering process section 14. The saturated hydrocarbon is then converted to an unsaturated hydrocarbon upon exposure to molten droplets 28 within process section 14.

One embodiment employs a method for converting a saturated hydrocarbon into an unsaturated hydrocarbon, as is described in U.S. Pat. No. 5,543,558. The teachings of U.S. Pat. No. 5,543,558, pertaining to the conversion of saturated hydrocarbons to unsaturated hydrocarbons, by exposure to molten transition metals, are incorporated herein by reference. Specifically, the organic component in the feed gas stream is exposed, in process section 14, to molten droplets 28 which include transition metals, particularly those having an energy gap between their ground and first excited electronic states of less than about 1.5 eV, such as rhodium.

Another embodiment uses a method for forming an unsaturated hydrocarbon, as is described in U.S. patent application Ser. No. 08/172,579, filed Dec. 23, 1993, which discloses a method for converting a saturated hydrocarbon into a shorter-chain unsaturated hydrocarbon through homolytic cleavage. The teachings of U.S. patent application Ser. No. 08/172,579, pertaining to the conversion of saturated hydrocarbons to shorter-chain unsaturated hydrocarbons, by exposure to molten transition metals having carbon solubility, are incorporated herein by reference. Specifically, the gasified organic feed component is exposed, in process section to molten droplets 28, which include transition metals, such as iron, chrome, vanadium, copper, aluminum, etc.

Yet another embodiment utilizes a method for forming an unsaturated hydrocarbon, as is described in U.S. patent application Ser. No. 08/173,346, filed Dec. 23, 1993, which discloses a method for converting a saturated hydrocarbon into a larger unsaturated hydrocarbon through homologation. The teachings of U.S. patent application Ser. No. 08/173,346, pertaining to the conversion of saturated hydrocarbons to larger unsaturated hydrocarbons, by exposure to molten transition metals, are incorporated herein by reference. Specifically, the gasified organic feed component is exposed in process section 14 to molten droplets 28 which also have a high carbon content, due to the addition of a carbon source, through alternate tuyere 54 into process molten bath 16. Suitable molten metals include transition metals, particularly those having an energy gap between their ground and first excited electronic states of less than about 1.5 eV, such as rhodium or copper.

The gasified organic feed component can be generated by any suitable method, such as the method described in U.S. Pat. No. 5,395,405 pertaining to the production of a gasified hydrocarbon by exposing an organic feed to a fountain of molten droplets.

Optionally, product gas directed from process section 14, and then through gas outlet 62, can then be introduced into one of more additional components for further treating the product gas and/or molten bath. This additional product gas process can include, for example, further enriching the amount of carbon oxide gas, or of a specific hydrocarbon, by exposing the product gas from a first process section to molten droplets 28 in a second process section. Other additional product gas process includes quenching reactions within the product gas, by directing the product gas through a suitable quenching means, purifying the product gas by directing the gas through a purification means, separating slag from a molten bath, generating a high quality condensed phase products by directing the product gas into a counter flow, plug flow furnace, and forming a new chemical species, such as ethylene or sulfuric acid, by directing the product gas through an appropriate regenerator furnace.

FIG. 4 illustrates another embodiment of this invention. The apparatus of FIG. 4 has many of the same elements of FIGS. 1 and 3 and like elements are designated with like numerals. Said apparatus includes reactor 12, containing gas formation section 64 and process section 14. Gas formation section 64 includes upper portion 88 and lower portion 89.

Retaining means 65, which extends from upper portion 88, is suitable for conducting a feed gas out of gas formation section 64, while retaining non-gasified solid feed within gas formation section 64. Retaining means 65 includes purifying means 90 and flow section 80, through which a gasified organic feed component pass prior to entering process section 14. Purifying means 90 is provided to physically and/or chemically separate impurities, such as condensible components, particulates or halogens, from the feed gas stream.

A suitable feed introduction means, such as lance 92, which can be consumable, is disposed at upper portion 88 of gas formation section 64. Lance 92 provides fluid communication between fluid feed source 94 and upper portion 88 of gas formation section 64 through fluid feed inlet 74. Fluid feed inlet 74 is disposed in upper portion 88 of gas formation section 64 at the end of lance 92.

A second feed introduction means, such as bulk feed inlet 76, extends from upper portion 88 of gas formation section 64. Bulk feed inlet 76 provides a means for directing bulky feed into gas formation section 64.

A third feed introduction means includes tuyere 96, which is disposed at lower portion 89 of gas formation section 64. Tuyere 96 is dimensioned and configured for introducing a feed, which can also function as a shroud gas, and a co-reactant into reactor 12. Tuyere 96 includes co-reactant inlet tube 50, which provides fluid communication between co-reactant source 52 and lower portion 89 of gas formation section 64 through co-reactant inlet 48. Co-reactant inlet 48 is disposed in lower portion 89 of gas formation section 64 at the end of co-reactant inlet tube 50.

Feed inlet tube 98 of tuyere 96 provides fluid communication between feed source 94 and lower portion 89 of gas formation section 64. Third feed inlet 100 is disposed in lower portion 89 of gas formation section 64 at the end of feed inlet tube 98.

Induction coil 102 is disposed at lower portion 89 of gas formation section 64 for heating gas formation molten bath 78 in gas formation section 64.

Trunions 104 can be disposed at gas formation section 64 for manipulation of gas formation section 64. Seal 106 is disposed between gas formation section 64 and retaining means 65 and is suitable for allowing partial rotation of gas formation section 64 about trunions 104 without breaking seal 106.

Gas formation molten bath 78 is disposed within gas formation section 64. Gas formation molten bath 78 is formed by partially filling gas formation section 64 with a suitable metal, metal compound, metal alloy or metal solution, or combinations therein. Gas formation molten bath 78 is then heated to a suitable temperature by activating induction coil 102 or by other means, not shown.

Gas formation gas space 66 is disposed over gas formation molten bath 78 and typically extends from upper portion 88 of gas formation section 64 through retaining means 65.

Gas stream introduction means includes gas stream tuyere 32, which is disposed at lower portion 89 of gas formation section 64. Gas stream tuyere 32 is dimensioned and configured for introducing a gas stream into reactor 12. Gas stream tuyere 32 includes gas stream inlet tube 108, which provides fluid communication between stream source 110 and lower portion 89 of gas formation section 64 through gas stream inlet 34. Gas stream inlet 34 is disposed in lower portion 89 of gas formation section 64 at the end of gas stream inlet tube 108.

Molten fountain 39 comprises a stream of molten drops of various sizes, which are disposed within gas formation gas space 66, that are directed out of gas formation molten bath 78 by the gas stream.

Optionally, ceramic layer 22 is disposed in gas formation section 64 on gas formation molten bath 78. In one embodiment, ceramic layer 22 is formed by directing suitable components, such as metals, metal oxides, halogens, sulfur, phosphorus, heavy metals, fluxes, sludges, etc., from flux source 24 through inlet tube 26 and onto and into gas formation molten bath 78 or from below the surface of gas formation molten bath 78. The components form oxides by exposure of the components to an oxidant, not shown, directed into gas formation section 64 or from other stable compounds at system conditions by reacting with other less stable components, such as alkali metal or alkaline earth metal cations.

Process molten bath 16 is disposed in lower portion of process section 14. Process molten bath 16 is formed by partially filling process section 14 with a suitable metal. The metal is then heated to a suitable temperature by activating plasma torches 20 or by other means, not shown. Plasma torches 20, which are disposed in the upper portion of process section 14, are suitable for maintaining process molten bath 16 in a molten state at a temperature suitable to convert a gasified organic feed component to a product gas. Plasma torches 20 are also suitable for atomizing molten metal to form molten droplets 28 which are dispersed, by the action of plasma torches 20, within process gas space 18 within process section 14.

Suitable co-reactant introduction means include co-reactant tuyeres 46, which are disposed in process section 14.

Alternate introduction means for directing a second feed, a fuel material for heating process molten bath 16, a carbon source and/or a gas stream suitable to provide an alternate means of dispersing molten droplets 28 within process gas space 18, include alternate tuyeres 54 and alternate inlets 56, which are disposed in process section 14.

In the method as shown in FIG. 4, in one embodiment feed is directed into at least one portion of the gas formation zone, specifically gas formation gas space 66, ceramic layer 22 and/or gas formation molten bath 78 by injecting the feed into upper portion 88 of gas formation section 64. The feed is directed from fluid feed source 94 through lance 92 into the gas formation zone through upper portion 88 of gas formation section 64. Alternately, feed is directed from fluid feed source 94, through tuyere 96, into gas formation molten bath 78. In yet another embodiment, bulk feed is directed into gas formation molten bath 78 through bulk feed inlet 76.

Upon injection of the feed, the feed gasifies, and/or is decomposed and partially gasifies, and/or reacts with a co-reactant to form a feed gas stream.

Subsequently, an inorganic impurity is separated from the feed gas stream being retained in ceramic layer 22 and/or gas formation molten bath 78 or by being subsequently removed by purifying means 90. The inorganic impurity can include metals, which could be retained in gas formation molten bath 78, light metals, or ceramic agents. A ceramic agent, as defined herein, is a condensible material that under the operating conditions of gas formation section 64 is not in its elemental form. Such agents include, for example, $SiO_2$, $Al_2O_3$, $Ca_s$, $CaF_2$, $Mg_3(PO_4)_2$, etc. The inorganic impurity can also contain metal salts, such as oxides, ash-forming substances, such as silicate or aluminate, sulfur and halogens which could be retained in ceramic layer 22.

Concurrent with the introduction of feed into gas formation section 64, a suitable gas stream of a nonreactive gas, such as nitrogen or argon, is directed from gas stream source 38 through gas stream inlet tube 36 into lower portion 89 of gas formation section 64. The gas stream then flows through gas formation molten bath 78, and ceramic layer 22, into gas formation gas space 66. The gas stream entrains molten drops and droplets 28, from gas formation molten bath 78, and thereby forms molten fountain 39 upon entering gas formation gas space 66.

Feed injected into gas formation section 64 is thereby exposed to molten metal in gas formation molten bath 78 and molten droplets 28 from molten fountain 39.

In a preferred embodiment, the gas stream comprises a second feed which contains a gasifiable component or decomposes to form a gasifiable component. Upon introduction of the second organic feed into gas formation molten bath 78, the second feed is gasified. The second gasified feed then migrates through gas formation molten bath 78 to form molten fountain 39 in gas formation gas space 66. Wherein the second organic feed contains a non-gasifiable impurity, the non-gasifiable impurity is retained in gas formation molten bath 78 or migrates into ceramic layer 22.

In another embodiment, an oxidant is directed as the co-reactant from co-reactant source 52 through co-reactant inlets 48 into gas formation molten bath 78. Upon injection, the oxidant will react with the feed and/or feed decomposition products to form gasified oxides such as carbon monoxide and/or carbon dioxide and water within the feed gas stream.

The gasified organic component within the feed gas stream contained in gas formation gas space 66 are then directed out of upper portion 88 of gas formation section 64, due to differential pressure, through retaining means 65, including purifying means 90 and flow section 80, into process gas space 18 within process section 14. Non-gasified solid feed, chemical impurities and physical impurities, such as condensibles, for example mercury and sulfur, particulates, and halogens are then separated from the gasified organic feed component.

Within process section 14, the discharge of plasma torches 20 are directed into process molten bath 16 to heat and atomize the molten metal and disperse molten droplets 28 across a cross-section of process gas space 18.

The feed gas stream from gas formation section 64 then flows through molten droplets 28, whereupon exposure to molten droplets 28 converts the organic component to form a product in at least one phase.

In another embodiment, an oxidant is directed as the co-reactant from co-reactant source 52 through co-reactant inlets 48 into process molten bath 16. Upon injection, the oxidant will react with the organic component of the feed as stream in process gas space 18 to form oxides such as carbon monoxide, carbon dioxide and water.

Any product gas is then directed out of upper portion of reactor 12 through gas outlet 62.

Figure 6:
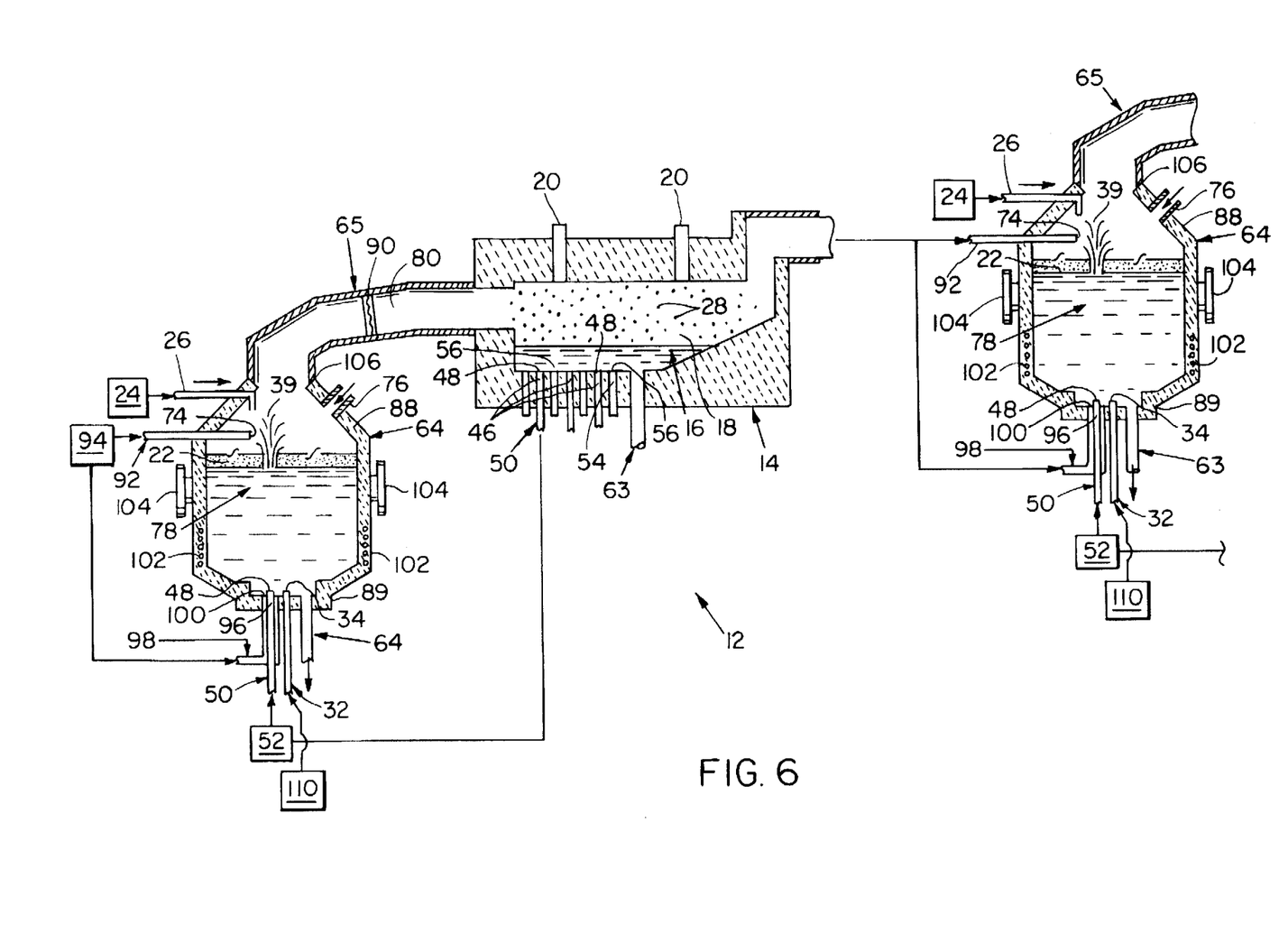
FIG. 6 is a cut-away side elevational illustration of yet another embodiment of an apparatus of the invention suitable for forming a product by directing a feed through a zone containing molten droplets.

In yet another embodiment, an additional gas forming section, as shown in FIG. 6, receives a product in at least one phase from the first process section to further convert the product by chemical reaction or purification means. The apparatus of FIGS. 5 and 6 has many of the same elements of the apparatus of FIGS. 3 and 4. In the method and apparatus of FIG. 6, an organic component in a feed gas stream is converted within the process section to form hydrogen gas and carbon, which is dissolved or entrained within the iron forming the process molten bath. The process molten bath is then tapped and directed into the molten bath within the second gas forming section. Concurrently, or subsequently, an oxidant is directed into the molten bath of the second gas formation section to oxidize the carbon and form carbon monoxide gas.

Equivalents

Those skilled in the art will recognize, or be able to ascertain using no more than routine experimentation, many equivalents to specific embodiments of the invention described specifically herein. Such equivalents are intended to be encompassed in the scope of the claims.

What is claimed is:

1. A method for converting a gaseous organic component of an organic feed gas stream, wherein said organic component is essentially gaseous, to form a product in at least one phase, comprising the steps of:

a) forming a process zone, wherein the process zone includes a process molten bath and a process gas space disposed over the process molten bath;

b) dispersing molten droplets of said molten bath across the process gas space;

c) directing the feed gas stream directly into the process gas space of the process zone, wherein the gaseous organic component is exposed to said molten droplets; and d) directing a co-reactant into the process molten bath, whereby the gaseous organic component reacts with the co-reactant to form a product in at least one phase.

2. A method of claim 1 wherein said molten droplets are dispersed by directing at least one gas stream through the process molten bath into the process gas space.

3. A method of claim 1 wherein said molten droplets are dispersed by directing at least one gas stream through the process gas space onto the surface of the process molten bath.

4. A method of claim 1 wherein the molten droplets are dispersed substantially uniformly within said process gas space.

5. A method of claim 1 wherein the organic-containing feed further includes at least one inorganic chemical.

6. A method of claim 1 wherein the product includes a gasified product in a gas phase, and further comprising the step of directing the gas phase product through a means for purifying said product.

7. A method of claim 1 wherein the product of processing the feed gas stream is a first product gas, and further comprising the steps of:
   a) forming a second process zone, wherein the second process zone includes a second process molten bath and a second process gas space disposed over the second process molten bath;
   b) dispersing molten droplets of the second molten bath across the second process gas space; and
   c) directing the first product gas through the second process gas space of the second process zone, whereby the first product gas is exposed to said molten droplets, thereby converting at least a portion of the first product gas to a second product gas.

8. A method of claim 7 wherein the molten metal droplets of the second molten bath remove at least a portion of an impurity from the first product gas, thereby converting the first product gas into the second product gas.

9. A method of claim 8 wherein the impurity includes a gaseous impurity.

10. A method of claim 8 wherein the impurity comprises a suspended impurity.

11. A method of claim 1, further comprising the step of exposing the organic-containing feed to gas forming means, whereby the organic-containing feed is converted to form the feed gas stream.

12. A method of claim 11 wherein the feed gas stream is formed by heating the organic-containing feed.

13. A method of claim 11 wherein the feed gas stream is formed by including particles of the organic component of the organic feed within a feed gas stream.

14. A method of claim 1 wherein the co-reactant includes a reducing agent.

15. A method of claim 14 wherein the organic component includes sulfur, wherein at least a portion of the sulfur is reduced to form hydrogen sulfide gas.

16. A method of claim 1 wherein the process zone contains a molten bath that includes a metal which has a free energy of oxidation that is greater than the free energy of oxidation of carbon to form carbon monoxide.

17. A method of claim 1 wherein the process zone contains a molten bath that includes a metal which has a free energy of chlorination which is greater than the free energy of chlorination of hydrogen to form hydrochloric acid.

18. A method of claim 1 wherein the process zone contains a molten bath having a carbon solubility of greater than about 0.5% by weight.

19. A method of claim 1 wherein the process zone contains a molten bath having a sulfur solubility of greater than about 0.5% by weight.

20. A method of claim 1 wherein the process zone contains a molten bath having a chlorine solubility of greater than about 0.5% by weight.

21. A method of claim 1 wherein the process zone contains a molten bath having an oxygen solubility of greater than about 0.5% by weight.

22. A method of claim 1 wherein the co-reactant is directed into the process gas space.

23. A method of claim 1 wherein the co-reactant includes an oxidant, whereby at least a portion of the organic feed component is oxidized to form an oxide.

24. A method of claim 11, further comprising the step of forming a gas formation zone, for forming the feed gas stream which is then directed into the process gas space to form the product.

25. A method of claim 23 wherein the oxidant is selected from the group consisting of oxygen, air, a metal oxide, carbon dioxide, and mixtures thereof.

26. A method of claim 24, further comprising the step of directing the organic-containing feed into the gas formation zone, wherein at least a portion of said organic-containing feed is treated to form the feed gas stream, which is then directed into the process gas space.

27. A method of claim 1 wherein at least two opposing gas streams are directed through the process gas space onto the surface of the process molten bath.

28. A method of claim 26 further including the step of directing a co-reactant into the gas formation zone, whereby at least a portion of the feed reacts with the co-reactant to form a feed gas stream.

29. A method of claim 28 wherein the co-reactant includes an oxidant, whereby at least a portion of the organic-containing feed is oxidized.

30. A method for converting a gaseous organic component of an organic feed gas stream, wherein said organic component is essentially gaseous, to form a product in at least one phase, comprising the steps of:
   a) forming a first process zone, wherein the first process zone includes a first process molten bath and a first process gas space disposed over the first process molten bath;
   b) dispersing molten droplets of said first molten bath across the first process gas space;
   c) directing the feed gas stream into the first process gas space of the first process zone, wherein the organic component is exposed to said molten droplets, thereby converting at least a portion of the organic component to a product in at least one phase;
   d) forming a second process zone, wherein the second process zone includes a second process molten bath and a second process gas space disposed over the second process molten bath;
   e) dispersing molten droplets of the second molten bath across the second process gas space; and
   f) directing a condensed phase component through a filtration means, said filtration means being located between the first process zone and the second process, and into said second process zone, thereby retaining a substantial portion of solid feed particles in the first process zone.

31. A method for converting a gaseous organic component of an organic feed gas stream, wherein said organic component is essentially gaseous, to form a product in at least one phase, comprising the steps of:
   a) forming a process zone, wherein the process zone includes a process molten bath and a process gas space disposed over the process molten bath;
   b) dispersing molten droplets of said molten bath across the process gas space;
   c) directing the feed gas stream directly into the process gas space of the process zone, wherein the gaseous organic component is exposed to said molten droplets, thereby converting at least a portion of the organic component to a product in at least one phase; and
   d) directing a reducing agent into the process zone, whereby the gaseous organic component reacts with the reducing agent to form a product in at least one phase.

32. A method of claim 31 wherein the organic component includes sulfur, wherein at least a portion of the sulfur is reduced to form hydrogen sulfide gas.

* * * * *